(12) United States Patent
Wijnant

(10) Patent No.: US 9,261,399 B2
(45) Date of Patent: Feb. 16, 2016

(54) METHOD AND DEVICE FOR DETERMINING ACOUSTIC COEFFICIENTS AND ACOUSTIC POWER

(75) Inventor: Ysbrand Hans Wijnant, Enschede (NL)

(73) Assignee: SoundInsight B.V., Enschede (NL)

( * ) Notice: Subject to any disclaimer, the term of this patent is extended or adjusted under 35 U.S.C. 154(b) by 860 days.

(21) Appl. No.: 13/509,568

(22) PCT Filed: Nov. 19, 2010

(86) PCT No.: PCT/NL2010/050776
§ 371 (c)(1),
(2), (4) Date: Aug. 2, 2012

(87) PCT Pub. No.: WO2011/062493
PCT Pub. Date: May 26, 2011

(65) Prior Publication Data
US 2012/0296600 A1   Nov. 22, 2012

(30) Foreign Application Priority Data

Nov. 19, 2009 (NL) ..................................... 2003832
Apr. 29, 2010 (NL) ..................................... 2004628

(51) Int. Cl.
| | | |
|---|---|---|
| G01L 11/04 | (2006.01) |
| G01H 3/10 | (2006.01) |
| G01H 9/00 | (2006.01) |
| G01H 3/12 | (2006.01) |
| G01N 29/46 | (2006.01) |

(52) U.S. Cl.
CPC . *G01H 3/10* (2013.01); *G01H 3/12* (2013.01); *G01H 9/002* (2013.01); *G01N 29/46* (2013.01)

(58) Field of Classification Search
USPC ........................................................ 702/138
See application file for complete search history.

(56) References Cited

U.S. PATENT DOCUMENTS

| | | |
|---|---|---|
| 3,915,016 A | 10/1975 | Jhaveri et al. |
| 4,655,086 A | 4/1987 | Mielnicka-Pate et al. |
| 5,679,899 A | 10/1997 | Webster et al. |
| 6,173,074 B1 | 1/2001 | Russo |

FOREIGN PATENT DOCUMENTS

NL          1008006 C1      7/1999

*Primary Examiner* — Paul D Lee
(74) *Attorney, Agent, or Firm* — Bret E. Field; Bozicevic, Field & Francis LLP

(57) ABSTRACT

A method for determining the acoustic absorption coefficient and/or the transmission coefficient at a chosen position in a space in which a certain sound field prevails as a result of the operation of a sound-emitting source, and/or the acoustic power emitted by the source comprises the following steps of:
(a) measuring the sound pressure p(t) and the particle velocity v(t) at the chosen position in the space;
(b) calculating the Fourier transforms P(f), V(f) of p(t), v(t);
(c) calculating on the basis of P(f) and V(f) the time-averaged active intensity Iac(f) in the direction indicated with the vector n, being the normal vector on the relevant surface, and the time-averaged total intensity Itot(f), in the direction indicated with the vector n;
(d) determining the time-averaged incident sound intensity in the direction n:

$Iin(f) = \frac{1}{2}(Iac(f) + Itot(f))$;

and the step of:
(e) determining the time-averaged absorption coefficient in the direction n:

$\alpha = Iac(f)/Iin(f)$;

and/or the step of:
(f) determining the transmission coefficient $\theta = Iac(f)/Iin(f)$ in the direction n for barriers wherein the mechanical absorption can be disregarded; and/or the steps of:
(q) defining an enveloping surface around the sound-emitting source; and
(r) determining the emitted acoustic power by integrating Iin(f) over the enveloping surface.

The invention also relates to a device for performing the method.

11 Claims, 1 Drawing Sheet

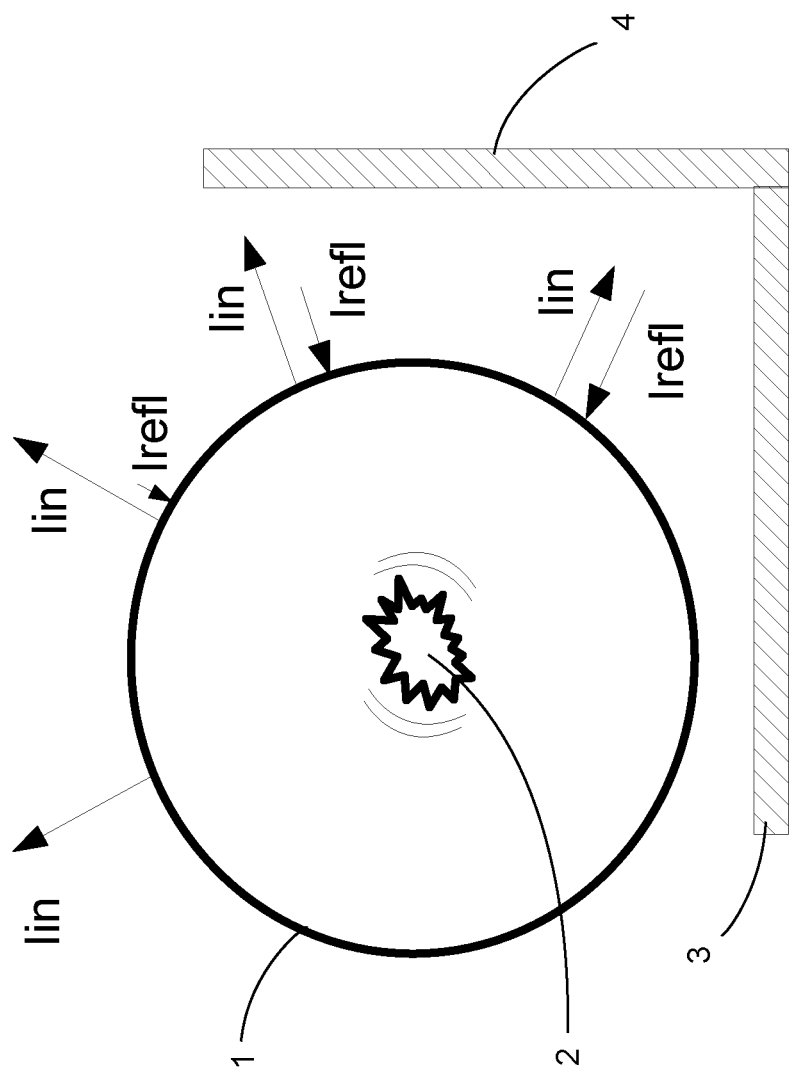

METHOD AND DEVICE FOR DETERMINING ACOUSTIC COEFFICIENTS AND ACOUSTIC POWER

The invention relates to a method and a device for determining the acoustic absorption coefficient and/or the acoustic transmission coefficient at a chosen position in a space in which a certain sound field prevails as a result of the operation of a sound-emitting source, and/or the acoustic power emitted by the source.

A measurement for determining the absorption coefficient of an (acoustic) material is generally known and usual. The absorption coefficient is defined as that fraction of the incident sound intensity/power that is absorbed by a determined surface at a determined position in a space. It can however only be measured by measuring the active sound intensity/power, i.e. the incident sound intensity/power minus the reflected sound intensity/power, and the incident sound intensity/power.

Such a measurement is problematic in practice and cannot always be performed in simple and rapid manner. Essential here is that, although the active sound intensity/power is measurable, determining the incident sound intensity/power has only been possible heretofore for several determined, known and simple sound fields, for instance flat waves, spherical waves or a diffuse sound field. This means that the measurement results obtained are applicable only for these sound fields. They are therefore not fully representative under all conditions for the results in practical conditions for random sound fields.

A measurement for determining the transmission coefficient of an acoustic barrier, for instance a panel, is less generally known. The transmission coefficient is defined as that fraction of the incident sound intensity/power that is transmitted at a determined position by a determined surface in a space. The transmission coefficient can also be measured only by measuring the active sound intensity/power and the incident sound intensity/power. Such a measurement is problematic in practice and cannot always be performed in simple and rapid manner. Here too it is essential that determining the incident sound intensity/power has only been possible heretofore for several determined, known and simple sound fields. Use is usually made of for instance an acoustic environment in which a panel, the transmission of which must be determined, is received in a window which forms the coupling between an acoustically hard, echoing space and a non-echoing space, usually referred to respectively as reverberant room and anechoic room. Such measurements, which can only be performed in a laboratory, are difficult and costly because very specific measurement setups are necessary. In addition, the obtained measurement results are not wholly representative under all conditions for the results realized with such a measured panel in practical conditions corresponding to a substantially diffuse sound field.

A measurement for determining the acoustic power emitted from an acoustic source is generally known and usual. It has however only been possible heretofore to determine the emitted acoustic power in a non-echoing space because, in the case of an echoing space, the emitted power determined in the usual manner is underestimated due to the acoustic reflections in the space. It can moreover be stated that emitted power determined in such a manner is not the power of the source in the situation where reflections from the environment are indeed present. The results obtained are therefore only applicable for the non-echoing situation and are not wholly representative under all conditions for the results in practical conditions. The usual manner of determining the emitted power of an acoustic source can therefore only be performed in a laboratory environment.

In the light of the above it is an object of the invention to provide a very simple measuring method and a device based thereon, which do not have the described drawbacks, are inexpensive and reliable, can be applied under realistic, even practical conditions and can thus be applied for a random sound field and can be implemented in the form of an easily portable apparatus having roughly the same physical dimensions and weight as a generally known and usual portable sound pressure meter or a sound intensity meter.

With a view to the above the invention provides a method for determining the acoustic absorption coefficient and/or the acoustic transmission coefficient at a chosen position in a space in which a certain sound field prevails as a result of the operation of a sound-emitting source, and/or the acoustic power emitted by the source, which comprises the following steps of:

(a) measuring the sound pressure $p(t)$ and the particle velocity $v(t)$ at the chosen position in the space;

(b) calculating the Fourier transforms $P(f)$, $V(f)$ of $p(t)$, $v(t)$;

(c) calculating on the basis of $P(f)$ and $V(f)$ the time-averaged active intensity $Iac(f)$ in the direction indicated with the vector n, being the normal vector on the relevant surface, and the time-averaged total intensity $Itot(f)$, in the direction indicated with the vector n;

(d) determining the time-averaged incident sound intensity in the direction n:

$$Iin(f)=(Iac(f)+Itot(f));$$

and the step of:

(e) determining the time-averaged absorption coefficient in the direction n:

$$\alpha=Iac(f)/Iin(f);$$

and/or the step of:

(f) determining the transmission coefficient $\theta=Iac(f)/Iin(f)$ in the direction n for barriers wherein the mechanical absorption can be disregarded; and/or the steps of:

(q) defining an enveloping surface around the sound-emitting source; and (r) determining the emitted acoustic power $Pin(f)$ by integrating $Iin(f)$ over the enveloping surface.

$Itot(f)$, the total intensity, is a quantity which has never been determined heretofore but which is however measurable in a random sound field.

The active or net intensity is the difference between the intensity of the incident wave and that of the reflected wave:

$$Iac(f)=Iin(f)-Irefl(f).$$

The total intensity is the sum of the intensity of the incident wave and that of the reflected wave:

$$Itot(f)=Iin(f)+Irefl(f).$$

This makes it possible to determine the absorption coefficient/transmission coefficient as according to (d), (e) and (f) and the emitted acoustic power as according to (q) and (r).

Vectors are shown with a symbol printed in bold and scalars are shown with a normally printed symbol.

In the above:
n=the direction vector pointing in the direction in which the absorption or transmission coefficient must be determined;
t=the time;
f=the frequency.

With a view to the above the invention also provides a method of the specified type, comprising the step of:

(g) performing step (c) on the basis of the relations:

$$Iac(f)=\tfrac{1}{4}(P\overline{V}\cdot n+\overline{P}V\cdot n)$$

and $$Itot(f)=\tfrac{1}{4}(\Delta c V\cdot n\overline{V}\cdot n+P\overline{P}(\Delta c)).$$

In the above:
$\overline{P}$=the complex conjugate of P;
$\overline{V}$=the complex conjugate of V;
$\Delta$=the density of the air;
c=the phase velocity or "speed of sound".

An alternative method of the specified type comprises the step of:

(h) calculating on the basis of P(f) and V(f) the time-averaged reactive intensity in the direction indicated with the vector n, i.e. $Ire(f)=\tfrac{1}{4}i(\overline{P}V\cdot n-P\overline{V}\cdot n)$;
and (i) performing step (c) on the basis of the relations:

$$Iac(f)=\tfrac{1}{4}(P\overline{V}\cdot n+\overline{P}V\cdot n)$$

and $$Itot(f)=(2/\pi)\arcsin(Iac(f)/\sqrt{(Iac(f)^2+Ire(f)^2)})$$
$$Iac(f)+\ldots+(2/\pi)|Ire(f)|$$

wherein $Ire(f)=\tfrac{1}{4}(\overline{P}V\cdot n-P\overline{V}\cdot n)$ is the reactive part of the intensity as determined in step (h).

The active and total sound intensity can also be determined using so-called cross-spectra and auto-spectra.

When the mechanical absorption of a panel is not negligible, the method can be extended by performing measurements on both sides of the panel and thus determining the mechanical absorption of the panel.

Use can be made in a so-called intensitometer. An intensitometer can comprise two pressure microphones, such as for instance in a Brüel & Kjaer intensity probe. Use can also be made of a Microflown® particle velocity meter in combination with a pressure microphone.

According to a following aspect, the invention provides a method comprising the steps of:

(j) measuring the sound pressure p(t) close to the surface in the space and the particle velocity v(t) at a number of chosen positions in the space;

(k) calculating the Fourier transforms P(f), V(f) of p(t), v(t);

(l) calculating on the basis of P(f) and V(f) the time-averaged active power Pac(f) obtained by integration of Iac(f), as determined under (g) or (I), over the relevant surface, wherein n is the normal vector on the relevant surface, and the time-averaged incident power Pin(f), obtained by integration of Iin(f), as determined under (d), over the relevant surface, wherein n is the normal vector on the relevant surface, (n) determining the spatially averaged absorption coefficient α=Pac(f)/Pin(f); and/or (o) determining the spatially averaged transmission coefficient θ=Pac(f)/Pin(f) for barriers wherein the mechanical absorption can be disregarded, (s) determining the emitted acoustic power by equating the emitted acoustic power with the incident power.

Alternatively, said method can comprise the step of:

(p) performing step (a) or step (j) by measuring the particle velocity v(t) using two pressure sensors which are disposed such that they together form a particle velocity sensor, and measuring the sound pressure p(t) with one or two of these two pressure sensors, in which latter case the average of the two sound pressures is determined.

Substantially the same results are obtained using such a variant. The advantage of this method is however that a pressure capsule is simpler and less expensive than a particle velocity sensor.

The invention further relates to a device for determining the acoustic absorption coefficient and/or the acoustic transmission coefficient and/or the acoustic power emitted by a source, the device forming an implementation of the above described method.

This device according to the invention comprises:
sound pressure measuring means for measuring the sound pressure p(t);
particle velocity measuring means for measuring the particle velocity v(t), which particle velocity measuring means are disposed in the immediate vicinity of the sound pressure measuring means;
Fourier transforming means for calculating the Fourier transforms P(f), V(f) of p(t), v(t);
first calculating means for calculating on the basis of p(t) and v(t) the active intensity Iac(f) and the time-averaged total intensity Itot(f); and
second calculating means for determining the incident intensity/the incident power, this latter being equal to the emitted acoustic power, and/or the time-averaged power Pac(f);
and
third calculating means for determining the absorption coefficient α=Iac(f)/Iin(f) and/or spatially averaged absorption coefficient α=Pac(f)/Pin(f) and/or transmission coefficient θ=Iac(f)/Iin(f) and/or spatially averaged transmission coefficient θ=Pac(f)/Pin(f).

This device can advantageously be embodied such that the particle velocity measuring means comprise two pressure sensors and the sound pressure measuring means comprise at least one of these two pressure sensors.

Other than in usual measuring methods for measuring absorption or transmission, it is not necessary according to the invention for use to be made of an acoustic source with specified properties. It is sufficient that a sound field be present in the space in which the measurement is performed, wherein the sound intensity is sufficient to enable performing of a significant measurement according to the invention.

For instance for measuring the absorption coefficient of a wall in a conference hall, a speaker, optionally assisted by a public address system, could function as source during the measurement. The performed measurement will then relate to the absorption coefficient in the relevant frequency domain of the human voice, for instance about 200 Hz-3 kHz.

It is possible to consider basing the measuring method for measuring absorption or transmission for specific applications on a normalized sound source. Referring to the foregoing discussion of a measurement of a conference hall, use can for instance be made of a noise-like source which can generate a sound field in the relevant space, the spectral composition of which on average corresponds at least roughly to that of the source to be applied in practice, for instance the above-mentioned speaker, which covers a frequency range of about 200 Hz-3 kHz.

It will be apparent that the Fourier transforming means can be based in per se generally known manner on a digital mathematical operation by means of a computer or microprocessor, such as Fast Fourier Transform or FFT. The further operations and calculations specified in the foregoing are also performed digitally by a processor.

To the third calculating means, which eventually calculate the absorption coefficient α or the transmission coefficient θ, can be added a signal output which generates a signal representative of the absorption coefficient for further processing and/or display. A display unit can for instance be applied, such as a meter or an LCD display or the like, on which the value of α or θ can be read at a glance.

It must be deemed essential for the measurement of absorption or transmission according to the invention that it is not necessary to apply a sound source with known properties. This is however still possible, whereby the measurement results can be specific to a determined application.

The determination of the acoustic power of a source, for instance a vibrating object, product, machine or the like, is currently done in specifically embodied acoustic environments. An associated measurement space must comply with well specified conditions, in particular be anechoic, semi-anechoic or echoic. Determining the emitted acoustic power in an in situ situation is not possible in the prior art. This is a result of the fact that it has not been possible heretofore to determine the effect of reflections by objects in the vicinity of the emitting source.

As specified above, it is possible according to the invention to calculate the active intensity Iac, the total intensity Itot, the incident intensity Iin in the reflected intensity Irefl at a random location in the space in a random direction. By now measuring the active intensity and the total intensity at a sufficient number of locations in an enveloping surface around the emitting source, the incident intensity at these locations can also be measured. As seen from the source, the incident intensity is equal to the emitted intensity. This implies that the power emitted by the source can be determined by integrating the incident intensity over the enveloping surface. The emitted power can thus be determined in the in situ situation.

The accompanying FIGURE illustrates this method. A source 2 emits sound. A virtual enveloping surface 1, for instance a sphere, is defined around source 2. The above stated intensities are indicated symbolically with arrows. It is noted here that in the shown random configuration two reflecting walls 3, 4 are arranged. The Iin and the associated Irefl are defined relative to wall 4. It will be apparent that in the vicinity of the reflecting objects, in this case the reflecting walls 3 and 4, Iac, being Iin–Irefl, substantially amounts to 0. At a distance from reflecting objects in the space Iac is greater and Irefl is smaller. The power emitted by source 1 in the in situ situation can now be determined by integrating Iin over the enveloping surface 2.

The invention claimed is:

1. A method for determining at least one of: the acoustic absorption coefficient of a material, the acoustic transmission coefficient of a material at a chosen position on a relevant surface in a space in which a certain sound field prevails as a result of the operation of a sound-emitting source, and the acoustic power emitted by the sound-emitting source, which method comprises the following steps of:
   (a) generating a sound with the sound-emitting source and measuring the sound pressure p(t) and the particle velocity v(t) at the chosen position in space;
   (b) calculating the Fourier transforms P, V of p(t), v(t) using a processor configured to calculate the Fourier transforms;
   (c) calculating on the basis of P and V using a processor the time-averaged active intensity Iac(f) in the direction indicated with the vector n, being a normal vector on the relevant surface, and the time-averaged total intensity Itot(f), in the direction indicated with the vector n;
   (d) determining using a processor the time-averaged incident sound intensity in the direction n:

$$Iin(f) = \tfrac{1}{2}(Iac(f) + Itot(f));$$

wherein:
   when the method comprises determining the acoustic absorption coefficient of a material the method further comprises: (e) determining the time-averaged absorption coefficient in the direction n:

$$\alpha = Iac(f)/Iin(f);$$

when the method comprises determining the acoustic transmission coefficient of a material the method further comprises: (f) determining the transmission coefficient θ=Iac(f)/Iin(f) in the direction n for materials wherein the mechanical absorption can be disregarded; and
   when the method comprises determining the acoustic power emitted by the sound-emitting source the method further comprises: (q) defining an enveloping surface around the sound-emitting source; and (r) determining the emitted acoustic power by integrating Iin over the enveloping surface.

2. The method as claimed in claim 1, comprising the step of:
   (g) performing step (c) on the basis of the relations:

$$Iac(f) = \tfrac{1}{4}(P\overline{V}\cdot n + \overline{P}V\cdot n)$$

and $$Itot(f) = \tfrac{1}{4}(\Delta c V \cdot n \overline{V}\cdot n + P\overline{P}(\Delta c));$$

wherein Δ is the density of the air and c is the phase velocity or speed of sound.

3. The method as claimed in claim 1, comprising the step of:
   (h) calculating on the basis of P and V the time-averaged reactive intensity in the direction indicated with the vector n, i.e. Ire(f)=¼ i($\overline{P}$V·n−P$\overline{V}$·n); and
   (i) performing step (c) on the basis of the relations:

$$Iac(f) = \tfrac{1}{4}(P\overline{V}\cdot n + \overline{P}V\cdot n)$$

and $$Itot(f) = (2/\pi)\arcsin(Iac(f)/\sqrt{(Iac(f)^2 + Ire(f)^2)})Iac(f) + \ldots + (2/\pi)|Ire(f)|$$

wherein Ire(f)=¼i($\overline{P}$V·n−P$\overline{V}$·n) is the reactive part of the intensity.

4. The method as claimed in claim 3, comprising the steps of:
   (j) measuring the sound pressure p(t) close to the surface in the space and the particle velocity v(t) at a number of chosen positions in the space;
   (k) calculating the Fourier transforms P, V of p(t), v(t);
   (l) calculating on the basis of P and V the time-averaged active power Pac(f) obtained by integration of Iac(f), as determined under step (i), over the relevant surface, wherein n is the normal vector on the relevant surface, and calculating the time-averaged incident power Pin(f), obtained by integration of Iin(f), as determined under (d), over the relevant surface, wherein n is the normal vector on the relevant surface, (n) determining the spatially averaged absorption coefficient $\alpha=\text{Pac}(f)/\text{Pin}(f)$; and/or (o) determining the spatially averaged transmission coefficient $\theta=\text{Pac}(f)/\text{Pin}(f)$ for materials wherein the mechanical absorption can be disregarded, (s) determining the emitted acoustic power by equating the emitted acoustic power with the incident power.

5. The method as claimed in claim 4, comprising the step of:

(p) performing step (a) or step (j) by measuring the particle velocity v(t) using two pressure sensors which are disposed such that together they form a particle velocity sensor, and measuring the sound pressure p(t) with one or two of these two pressure sensors, in which latter case the average of the two sound pressures is determined.

6. A device for determining the acoustic absorption coefficient, the acoustic transmission coefficient or the acoustic power emitted by a source with a method as claimed in claim 1, the device comprising:

a sound pressure measurer for measuring the sound pressure p(t);

a particle velocity measurer for measuring the particle velocity v(t), which particle velocity measurer is disposed in the immediate vicinity of the sound pressure measurer;

a Fourier transformer for calculating the Fourier transforms P, V of p(t), v(t);

first calculator for calculating on the basis of p(t) and v(t) the time-averaged active intensity Iac(f) and the time-averaged total intensity Itot(f); and a second calculator for determining the time-averaged active intensity Iac(f) and for determining the incident intensity Iin(f); and a third calculator for determining the absorption coefficient $\alpha=\text{Iac}(f)/\text{Iin}(f)$ and/or transmission coefficient $\theta=\text{Iac}(f)/\text{Iin}(f)$.

7. The device as claimed in claim 6, wherein the particle velocity measurer comprises two pressure sensors and the sound pressure measurer comprises at least one of these two pressure sensors.

8. The method as claimed in claim 1, further comprising generating a signal representative of the absorption coefficient, transmission coefficient or emitted acoustic power with a signal output.

9. The method as claimed in claim 8, further comprising displaying the signal on a display unit.

10. The method as claimed in claim 1, further comprising arranging a reflecting wall.

11. The method as claimed in claim 1, wherein the method comprises arranging the material at a distance from the sound-emitting source.

* * * * *